United States Patent [19]

Shoesmith, deceased

[11] Patent Number: Plant 5,983

[45] Date of Patent: May 12, 1987

[54] CHRYSANTHEMUM PLANT NAMED CALICO

[75] Inventor: Leonard H. Shoesmith, deceased, late of Westfield, England, by May V. Shoesmith, executrix

[73] Assignee: Ball Pan Am Plant Company, Parrish, Fla.

[21] Appl. No.: 712,691

[22] Filed: Mar. 18, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Chrysanthemum named Calico having a dwarf habit, flat capitulum form and anemone capitulum type, red-bronze flower color, eight week response, and an ability to be grown year around in 9 cm. pots with little growth regulation.

1 Drawing Figure

The present invention comprises a new and distinct cultivar of *Chrysanthemum morifolium,* Ramat., hereinafter referred to by the cultivar name Calico.

Calico is a product of a planned breeding program which had the objective of creating new Chrysanthemum cultivars with eight (8) week response, red bronze anemone type flowers, and dwarf habit suitable for year around growing in 9 cm. pots. Such traits in combination were not present in previously available commercial cultivars.

Calico was originated from a hybridization made by Leonard H. Shoesmith in a controlled breeding program in Westfield, Woking, England in 1977. The male and female parents are unknown at this time. Calico was discovered and selected as one flowering plant within the progeny of the parentage by applicant in November, 1978 in a controlled environment in West Chicago, Ill., and given the code name F8-315-BS.

The first act of asexual reproduction of Calico was accomplished when vegetative cuttings were taken from the initial selection in February, 1979 in a controlled environment in West Chicago, Ill. by a technician working under formulations established and supervised by Leonard H. Shoesmith. Horticultural examination of selected units initiated in March, 1979 has demonstrated that the combination of characteristics as herein disclosed for Calico are firmly fixed and are retained through successive generations of asexual reproduction.

Calico has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Calico, which in combination distinguish this Chrysanthemum as a new and distinct cultivar:

1. Flat capitulum form.
2. Anemone capitulum type.
3. Red-bronze flower.
4. Dwarf habit, extending 10–15 cm. above edge of pot.
5. Eight (8) week response.

6. Ability to be grown year around in 9 cm. pots in most areas, and requiring few B-9 treatments.

Of the many commercial cultivars known to the present inventor, the most similar in comparison to Calico is the cultivar Cherub, disclosed in U.S. Plant Pat. No. 4,629. In comparison to Cherub, Calico has a red bronze color, has stronger stems, has one (1) week earlier response, and is more dwarf and suitable for year round growing in 9 cm. pots. The flower form and type of Calico are similar to those same characteristics of Cherub.

The accompanying photographic drawing shows typical inflorescense characteristics of Calico. The photograph is in black and white except for one flower, which is colored to precisely show the ray and disc floret colors.

In the following description color references are made to The Royal Horticultural Society Colour Chart. The color values were determined at approximately 11:00 a.m. on Jan. 17, 1985 under natural and fluorescent light at Bradenton, Fla.

Classification:

*Botanical.*—*Chrysanthemum morifolium,* Ramat., CV Calico.

*Commercial.*—Anemone, four (4) inch pot.

I. INFLORESCENCE

A. Capitulum:

*Form.*—Flat.

*Type.*—Anemone.

*Diameter across face.*—3–5 cm.

B. Corolla of ray florets:

*Color (general tonality from a distance of three meters).*—Dark red-bronze ray; disc corolla looks golden on edges.

*Color (top surface).*—180A on fresh fully opened petal; tubes yellow-orange prior to opening to form petal.

*Color (under surface).*178 B.

C. Corolla of disc floret:

*Color (mature).*—178 B with gold edges on corolla tube.

*Color (immature).*—178 B.

D. Reproductive organs:

*Androecium.*—Present in disc florets only; numerous.

*Gynoecium.*—Present in both ray and disc florets; numerous.

II. PLANT

A. General appearance:

*Height.*—10–15 cm. above edge of pot when properly grown in 9 cm. pot.

B. Foliage:

*Color* (*under surface*).—147 B.

*Color* (*top surface*).—147 A.

*Shape.*—Ovate and deeply lobed.

It is claimed:

1. A new and distinct cultivar of Chrysanthemum named Calico, as described and illustrated, and particularly characterized by its dwarf habit; flat capitulum form and anemone capitulum type; red-bronze flower color; eight week response, and by its ability to be grown year around in 9 cm. pots with little growth regulation.

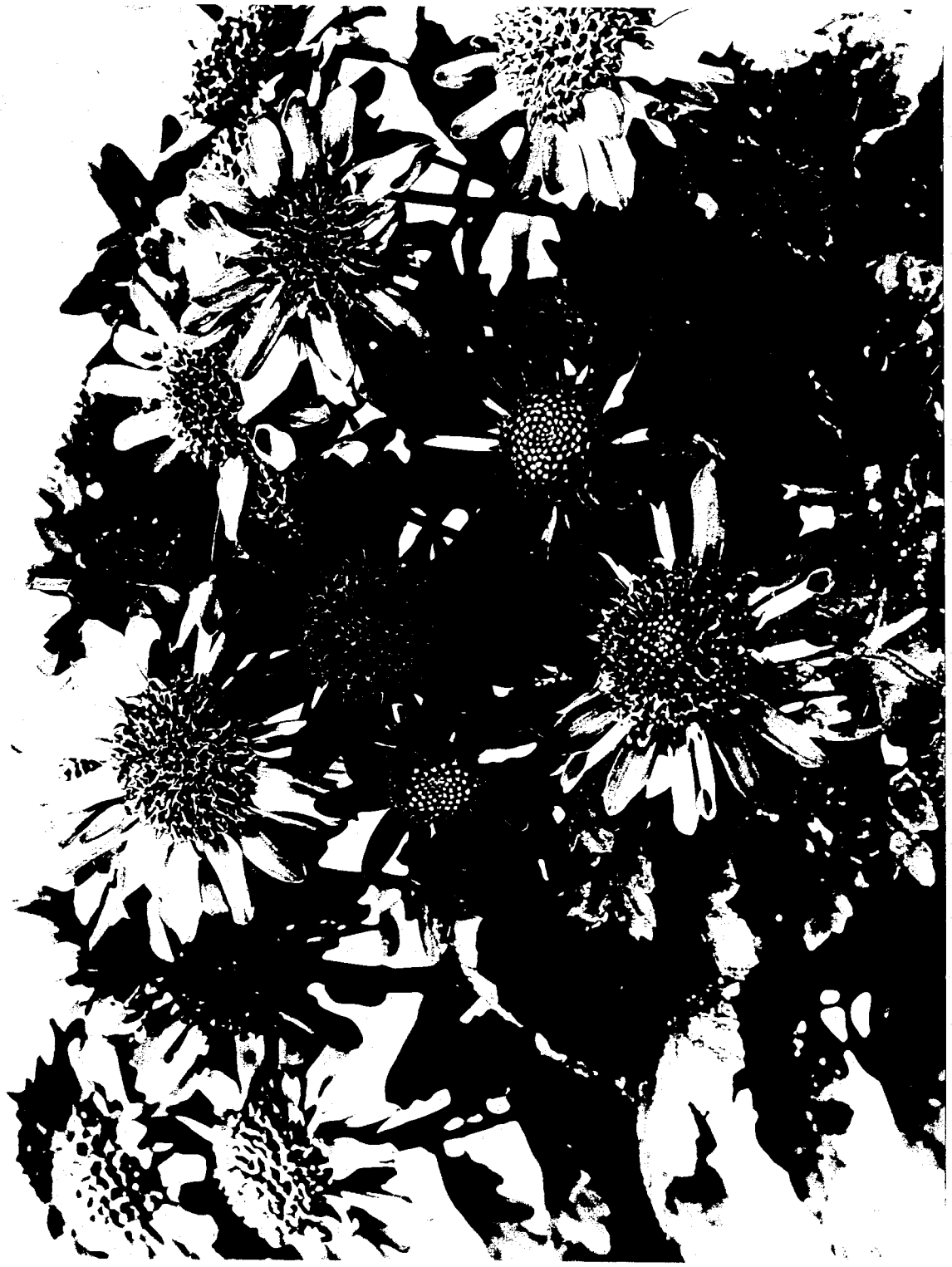

* * * * *